United States Patent
Garcia et al.

(10) Patent No.: US 11,110,007 B2
(45) Date of Patent: Sep. 7, 2021

(54) OPHTHALMIC LASER SURGICAL METHOD AND SYSTEM FOR FORMING CORNEAL LENTICULE WITH SIDE TAB FOR EASY EXTRACTION

(71) Applicant: AMO Development, LLC, Santa Ana, CA (US)

(72) Inventors: Jose L. Garcia, Fremont, CA (US); Griffith E. Altmann, Ladera Ranch, CA (US)

(73) Assignee: AMO Development, LLC, Santa Ana, CA (US)

( * ) Notice: Subject to any disclaimer, the term of this patent is extended or adjusted under 35 U.S.C. 154(b) by 152 days.

(21) Appl. No.: 16/355,642

(22) Filed: Mar. 15, 2019

(65) Prior Publication Data

US 2020/0289320 A1    Sep. 17, 2020

(51) Int. Cl.
*A61F 9/008*    (2006.01)
*A61B 18/00*    (2006.01)

(52) U.S. Cl.
CPC    *A61F 9/00827* (2013.01); *A61B 2018/00601* (2013.01); *A61F 2009/00872* (2013.01); *A61F 2009/00897* (2013.01)

(58) Field of Classification Search
CPC ....... A61F 9/00827; A61F 2009/00872; A61B 2018/00601
See application file for complete search history.

(56) References Cited

U.S. PATENT DOCUMENTS

| | | | |
|---|---|---|---|
| 4,764,930 A | 8/1988 | Bille et al. | |
| 5,196,027 A * | 3/1993 | Thompson | A61F 9/00804 128/898 |
| 5,993,438 A | 11/1999 | Juhasz et al. | |
| 6,110,166 A | 8/2000 | Juhasz | |
| 6,315,413 B1 | 11/2001 | Shimmick et al. | |
| 6,599,305 B1 | 7/2003 | Feingold | |
| 8,260,024 B2 | 9/2012 | Farrer et al. | |

(Continued)

FOREIGN PATENT DOCUMENTS

CA    2331223 C    8/2011

OTHER PUBLICATIONS

Co-pending U.S. Appl. No. 16/121,482, filed Apr. 9, 2018.
International Search Report and Written Opinion for Application No. PCTIB2020052213, dated May 29, 2020, 6 pages.

*Primary Examiner* — Gary Jackson
*Assistant Examiner* — Zahed Kabir
(74) *Attorney, Agent, or Firm* — Johnson & Johnson Surgical Vision, Inc.

(57) ABSTRACT

In an ophthalmic laser procedure, a lenticule is formed in the cornea and extracted from the cornea to accomplish vision correction. The ophthalmic laser system is used to form top and bottom lenticule incisions which intersect each other to form an isolated volume of corneal tissue in between. The volume of tissue includes a lenticular portion having a circular or oval shape and a side tab that protrudes from the peripheral of the lenticular portion. The side tab has a radial dimension between 0.5 and 5 mm and a width between 0.5 and 3 mm in. An entry cut is further formed from the anterior corneal surface to the top or bottom lenticule incisions to provide access to the lenticule. During extraction, the surgeon uses the surgical tool to grab the side tab to extract the lenticule.

18 Claims, 6 Drawing Sheets

(56) References Cited

U.S. PATENT DOCUMENTS

| | | |
|---|---|---|
| 9,833,358 B2 | 12/2017 | Schuele et al. |
| 2011/0224657 A1 | 9/2011 | Stevens et al. |
| 2011/0319876 A1* | 12/2011 | Feingold ............. A61F 9/00836 606/4 |
| 2012/0016351 A1 | 1/2012 | Stobrawa et al. |
| 2014/0155871 A1* | 6/2014 | Cumming ............... A61F 2/142 606/5 |
| 2015/0230981 A1 | 8/2015 | Kahook et al. |
| 2015/0374548 A1* | 12/2015 | Wottke ................ A61F 9/00827 606/5 |
| 2016/0089270 A1 | 3/2016 | Fu |
| 2017/0087021 A1 | 3/2017 | Dishler et al. |
| 2018/0243128 A1* | 8/2018 | Jung .................. A61F 9/00827 |
| 2019/0060122 A1 | 2/2019 | Fu et al. |
| 2020/0206033 A1* | 7/2020 | Dishler ............... A61F 9/00827 |

* cited by examiner

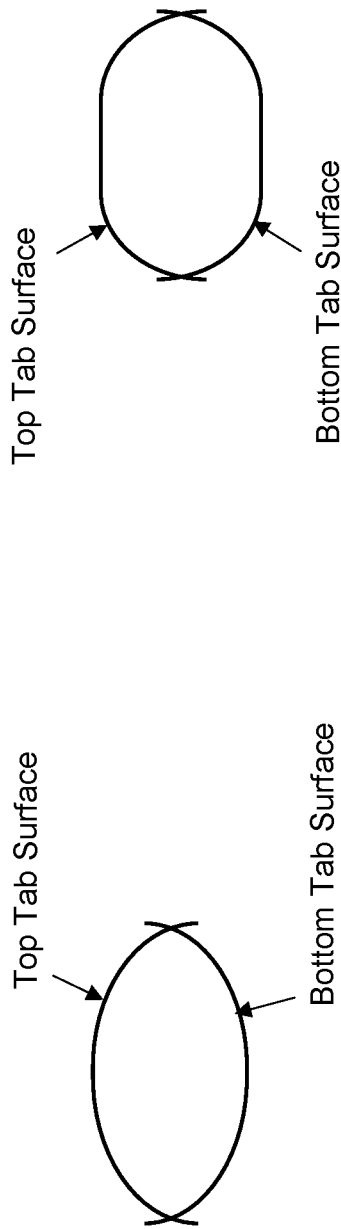
Fig. 2C-1
Fig. 2C-2
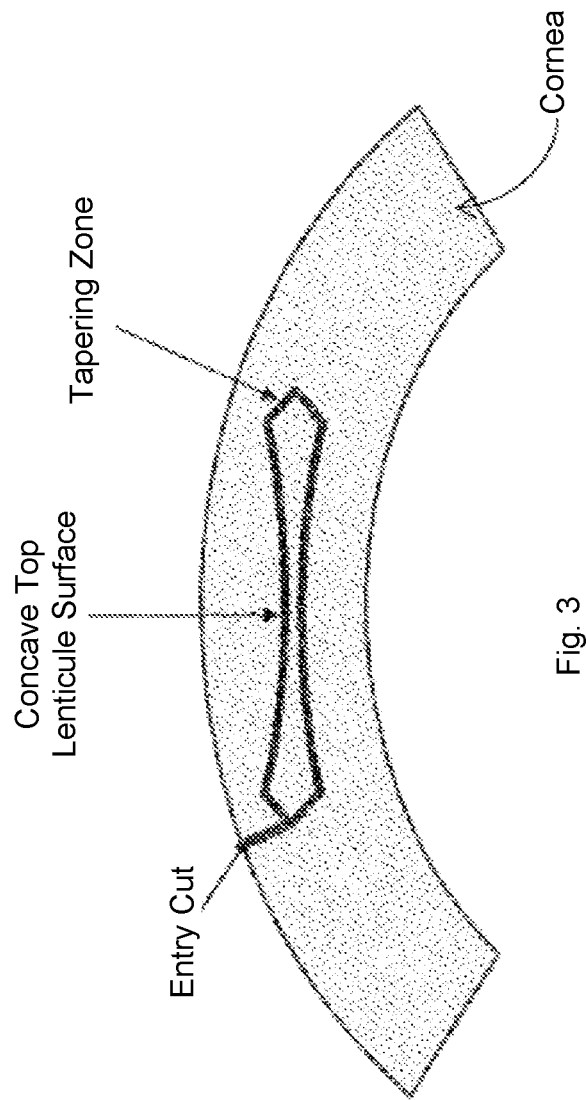
Fig. 3

OPHTHALMIC LASER SURGICAL METHOD AND SYSTEM FOR FORMING CORNEAL LENTICULE WITH SIDE TAB FOR EASY EXTRACTION

BACKGROUND OF THE INVENTION

Field of the Invention

Embodiments of this invention relate generally to laser-assisted ophthalmic procedures, and more particularly, it relates to methods and systems for lenticular incisions in the cornea and lenticule extraction.

Description of Related Art

Vision impairments such as myopia (near-sightedness), hyperopia and astigmatism can be corrected using eyeglasses or contact lenses. Alternatively, the cornea of the eye can be reshaped surgically to provide the needed optical correction. Eye surgery has become commonplace with some patients pursuing it as an elective procedure to avoid using contact lenses or glasses to correct refractive problems, and others pursuing it to correct adverse conditions such as cataracts. And, with recent developments in laser technology, laser surgery is becoming the technique of choice for ophthalmic procedures.

Different laser eye surgical systems use different types of laser beams for the various procedures and indications. These include, for instance, ultraviolet lasers, infrared lasers, and near-infrared, ultra-short pulsed lasers. Ultra-short pulsed lasers emit radiation with pulse durations as short as 10 femtoseconds and as long as 3 nanoseconds, and a wavelength between 300 nm and 3000 nm.

Prior surgical approaches for reshaping the cornea include laser assisted in situ keratomileusis (hereinafter "LASIK"), photorefractive keratectomy (hereinafter "PRK") and Small Incision Lens Extraction (hereinafter "SmILE"). In the SmILE procedure, instead of ablating corneal tissue with an excimer laser following the creation of a corneal flap, the technique involves tissue removal with two femtosecond laser incisions that intersect to create a lenticule for extraction. The extraction of the lenticule changes the shape of the cornea and its optical power to accomplish vision correction. Lenticular extractions can be performed either with or without the creation of a corneal flap. With the flapless procedure, a refractive lenticule is created in the intact portion of the anterior cornea and removed through a small incision.

SUMMARY OF THE INVENTION

To obviate one or more problems due to limitations and disadvantages of the related art, embodiments of the present invention provide a method for extracting a lenticule from a cornea of a patient's eye, the method including: operating an ophthalmic surgical laser system to form a top lenticule surface incision in the cornea; and operating the ophthalmic surgical laser system to form a bottom lenticule surface incision in the cornea, wherein the top and bottom lenticule surface incisions intersect each other to form a volume of corneal tissue between them, and wherein the volume of corneal tissue includes a lenticular portion having a circular or oval shape in a top view, and a side tab portion connected to the lenticular portion and protrudes from a peripheral location of the lenticular portion, wherein the side tab portion has a defined thickness profile in a side cross-sectional view. In some embodiments, the side tab portion has a length in a radial direction between 0.5 and 5 mm and a width in an angular direction between 0.5 and 3 mm in the top view, and a tapered thickness in the side cross-sectional view.

In another aspect, the present invention provides an ophthalmic surgical laser system for forming a lenticule in a cornea of a patient's eye for extraction, the system including: a laser system configured to generate a pulsed laser beam; an optical delivery system configured to deliver the published laser beam to a cornea of a patient's eye, including a scanner system configured to scan a focus spot location of the pulsed laser beam within the cornea; a controller configured to control the laser system and the scanner system to: scan the focus spot location of the pulsed laser beam within the cornea to form a top lenticule surface incision in the cornea; and scan the focus spot location of the pulsed laser beam within the cornea to form a bottom lenticule surface incision in the cornea, wherein the top and bottom lenticule surface incisions intersect each other to form a volume of corneal tissue between them, and wherein the volume of corneal tissue includes a lenticular portion having a circular or oval shape in a top view, and a side tab portion connected to the lenticular portion and protrudes from a peripheral location of the lenticular portion, wherein the side tab portion has a defined thickness profile in a side cross-sectional view.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

The novel features of the invention are set forth with particularity in the appended claims. A better understanding of the features and advantages will be facilitated by referring to the following detailed description that sets forth illustrative embodiments using principles of the invention, as well as to the accompanying drawings, in which like numerals refer to like parts throughout the different views. Like parts, however, do not always have like reference numerals. Further, the drawings are not drawn to scale, and emphasis has instead been placed on illustrating the principles of the invention. All illustrations are intended to convey concepts, where relative sizes, shapes, and other detailed attributes may be illustrated schematically rather than depicted literally or precisely.

FIGS. 2C-1 and 2C-2 illustrate exemplary cross sectional views of the side tab along the direction 2C-2C' in FIGS. 1 and 2B.

FIG. 3 schematically illustrates a corneal lenticule having concave top and bottom surfaces.

DETAILED DESCRIPTION OF PREFERRED EMBODIMENTS

Embodiments of this invention are generally directed to systems and methods for laser-assisted ophthalmic procedures, and more particularly, to methods and systems for corneal lenticule formation and extraction. More specifically, the corneal lenticule is formed with a generally circular or oval shape with a side tab that protrudes from the periphery of the lenticule to assist in easy extraction of the lenticule from the cornea.

Figure 1:
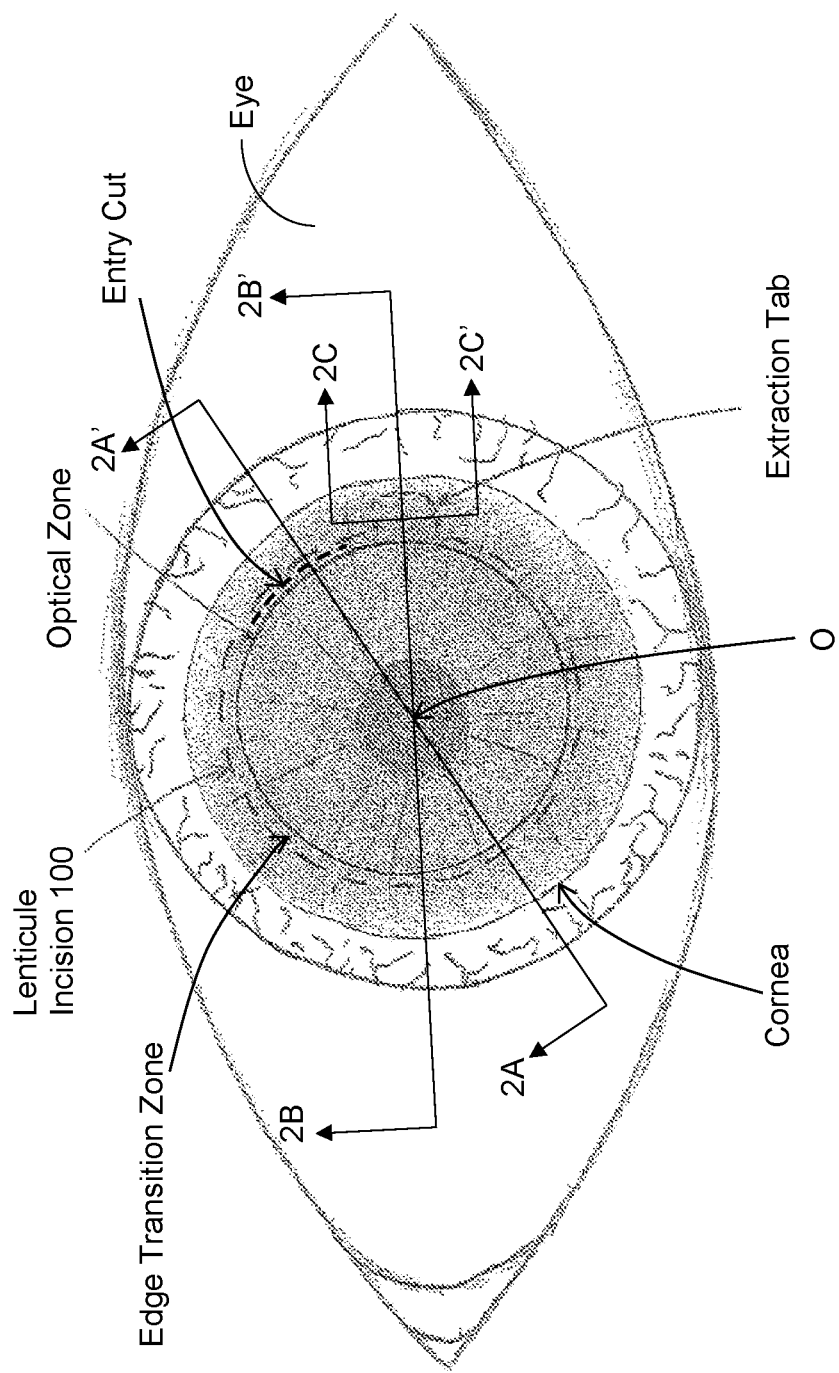
FIG. 1 is a top view schematically illustrating a corneal lenticule according to an embodiment of the present invention.
Figure 2A:
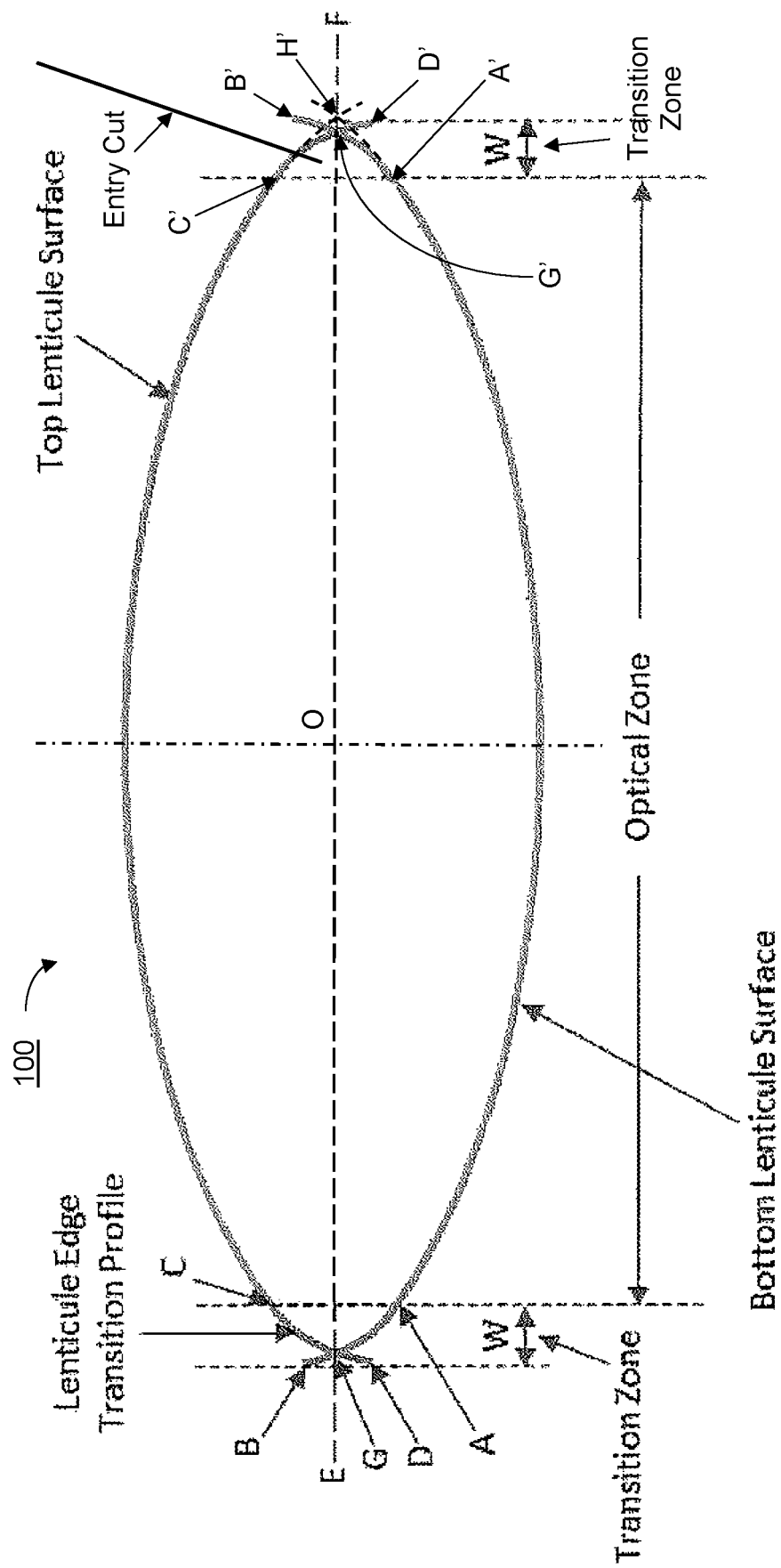
FIGS. 2A and 2B illustrate side cross sectional views of the corneal lenticule incision of FIG. 1 along the directions 2A-2A' and 2B-2B', respectively.
Figure 2B:
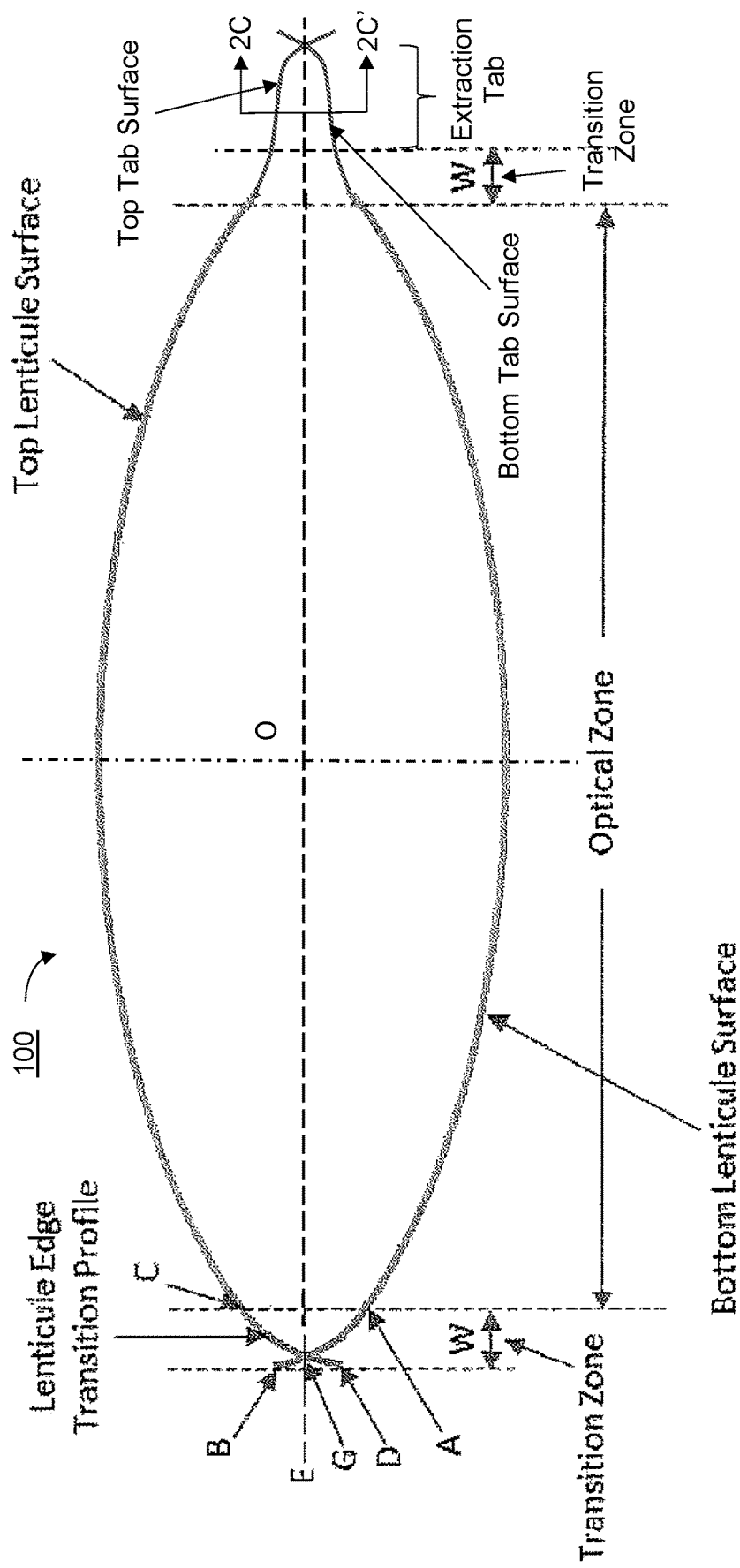

FIGS. 1, 2A, 2B, 2C-1 and 2C-2 schematically illustrate the shape of a corneal lenticule according to embodiments of the present invention. FIG. 1 is a top (front) view showing the eye, the cornea, and the lenticule having a side tab (extraction tab), viewed in a direction parallel to the optical axis O of the eye. FIGS. 2A and 2B are side cross-sectional views of the lenticule in respective planes passing through the optical axis O, viewed in the directions 2A-2A' and 2B-2B' of FIG. 1, respectively. The cross-section shown in FIG. 2A does not include the side tab, and the cross-section shown in FIG. 2B includes the side tab.

In FIGS. 2A and 2B, the vertical direction is the depth direction of the eye, parallel to the optical axis O, and the horizontal direction is referred to as the transverse direction. The cornea from which the lenticule is incised and extracted is not shown in FIGS. 2A and 2B. In this embodiment, the incisions are performed while the cornea is flattened (applanated) by a contact lens (not shown) of a patient interface device of the laser system which presses against and flattens the cornea.

As shown in FIG. 1, the lenticule 100 preferably has a circular or oval shape in the top view, except for the side tab that protrudes from a peripheral location of the lenticule. As shown in FIG. 2A, the lenticule 100 is formed by a top lenticular incision surface D-C-C'-D' and a bottom lenticular incision surface B-A-A'-B', which intersect each other at the peripheral edge of the lenticule, shown as points G and G' in the cross-sectional view. The intersecting top and bottom surfaces form an isolated volume of the cornea which constitutes the lenticule. Preferably, the end points D and B of the top and bottom edge transition portions CD and AB extend beyond the intersection point G of the two edge transition portions. This helps to ensure that the lenticule is fully separated from the cornea, so that the extraction can be done free of tissue-bridges and minimal or no unwanted residual tissue pieces are left inside the cornea.

In the illustrated embodiment, both top and bottom surfaces are convex, and the lenticule is a convex lens shape. Extracting this lenticule from the cornea effectuates a myopia correction of the eye.

Each of the top and bottom lenticular surfaces has a spherical portion CC' or AA' at the center, referred to as the optical zone, and a peripheral portion CD and C'D' or AB and A'B' that extends beyond the spherical portion, referred to as the edge transition zone. In the top view, the spherical portion preferably has a circular or oval shape and the edge transition zone has a circular or oval ring shape that surrounds the spherical portion. In the top view, the top and bottom spherical portions overlap each other and the top and bottom edge transition portions overlap each other. While each of the top and bottom spherical portions CC' and AA' is a part of a sphere, the respective edge transition zone is not located on the same sphere of the spherical portion but rather, has a steeper shape in the side cross-sectional view than the sphere. In other words, each edge transition zone is located inside of the volume defined by the sphere of the corresponding spherical portion. Thus, the distance from the optical axis O of the lenticule to the intersection point G, where the top edge transition portion CD and the bottom edge transition portion AB intersect each other, is smaller than the distance from the optical axis O to the imaginary intersection point H' where the two spheres that define the spherical portions CC' and AA' intersect each other, as shown in FIG. 2A. In FIG. 2A, the two intersection points are illustrated on the right-hand side edge of the lenticule 100 and labeled G' and H', respectively, where OG'<OH'.

In some embodiments, the radial dimension of transition zone is approximately 0.5-2.0 mm, depending on size of optical zone.

The provision of the transition zone is optional. In other words, the entire top and bottom lenticule surfaces D-C-C'-D and B-A-A'-B' may be spherical surfaces forming the optical zone.

The side tab of the lenticule is formed to assist in easy extraction of the lenticule from the cornea. As shown in FIGS. 1 and 2B, the side tab is located at a defined angular position along the periphery of the lenticule, preferably temporally located (i.e. on the temple side) for easier access, but may alternatively be located anywhere along the periphery of the lenticule. In some embodiments, the side tab is substantially rectangular in the top view (FIG. 1) with a size of approximately 0.5-5 mm in the radial direction of the lenticule and approximately 0.5-3 mm in the angular direction of the lenticule. The size of the side tab is chosen based on considerations of the size of the lenticule (which is typically 4.5 to 9 mm in diameter including the transition zone) and the sizes of the extraction tool. In alternative embodiment, the side tab may have a slightly tapered shape in the top view, being narrower at the outer edge. In the side cross-sectional plane that passes through the optical axis O (FIG. 2B), the side tab has a profile that has a generally tapered thickness and a rounded outer edge.

The side tab is formed by a top side tab surface which is a part of the top lenticule surface and is smoothly connected to the rest of the top lenticule surface (e.g. the edge transition zone), and a bottom surface which is a part of the bottom lenticule surface and is smoothly connected to the rest of the bottom lenticule surface (e.g. the edge transition zone), the top and bottom side tab surfaces intersecting each other to form the outer edge of the side tab. As described earlier, the edge transition zones has a steeper shape in the side cross-sectional view than the sphere of the optical zone; in the area corresponding to the side tab, however, the edge transition zones is made less steep than the sphere, and the top and bottom side tab surfaces continue to extend outwardly beyond where the imaginary intersection point of the top and bottom spheres.

In a cross-section cutting through the side tab by a plane that is parallel to the optical axis O (see the line with arrows 2C-2C' in FIG. 2B) and tangential to the peripheral circle of the lenticule (see the line with arrows 2C-2C' in FIG. 1), the side tab may have a substantially oval shape, as shown in the example of FIG. 2C-1, or a shape with substantially flat top and bottom and rounded sides, as shown in the example of FIG. 2C-2, of a shape with concave top and bottom and rounded sides (not shown in drawings), or other suitable shapes.

As shown in the examples in FIGS. 2B, 2C-1 and 2C-2, the top and bottom side tab surfaces preferably extend beyond where they intersect each other, which helps to ensure that the side tab is fully separated from the cornea.

Preferably, the entire top lenticular surface, including the top side tab surface, is a smooth surface and the entire bottom lenticular surface, including the bottom side tab surface, is a smooth surface. This reduces tissue step formation in the cornea after the lenticule is extracted.

In corneal lenticule extraction procedures, an entry cut is also formed to provide an access of extraction tools and a passage for lenticule removal. The entry cut is typically a band shape which extends from the anterior cornea surface to the top (or bottom) lenticule surface at a location within the transition zone, as shown in FIGS. 1 and 2A. The intersection line of the entry cut with the top (or bottom) lenticule surface is typically an arc shape as schematically shown by the dashed arc in FIG. 1. In the top view, the angular position of the intersection of the entry cut with the top or bottom lenticule surface is preferably in a vicinity of the side extraction tab, for example, with a gap of less than a few mm between them. The entry cut and the side tab may also overlap each other in the top view.

In a corneal lenticule extraction procedure, after forming the top and bottom lenticule surfaces including the side tab, and the entry cut, the surgeon inserts a surgical tool, such as a surgical spatula or surgical tweezers, through the entry cut, to separate the lenticule tissue at the top and bottom lenticule surfaces from the remaining cornea tissue. The surgeon then uses the same or another surgical tool to grab the side tab and extract the lenticule from the cornea through the entry cut.

In the embodiment shown in FIGS. 2A and 2B, both top and bottom surfaces are convex. In alternative embodiments, one or both of the top and bottom surfaces may be concave, and the lenticule may be a convex or concave lens shape. For example, in the lenticule shown in FIG. 3, both the top and the bottom surfaces are concave and the lenticule is a concave lens shape.

Formation of a corneal lenticule without a side extraction tab is described in co-pending U.S. Pat. Appl. Pub. No. 20190060122, published Feb. 28, 2019, entitled Systems and Methods for Lenticular Laser Incision, and U.S. patent application Ser. No. 16/121,482, filed Sep. 4, 2018, entitled Ophthalmic Laser Surgical System and Method for Corneal Lenticular Incisions with Unambiguous Entry Cuts, the disclosures of which are incorporated herein in their entireties. For a corneal lenticule formed without a side tab, extraction of the lenticular tissue is sometimes difficult. Surgeons typically use surgical tweezers to remove the lenticule. During extraction, the transition zone outside of the optical zone may be grabbed to extract the corneal tissue. However, there is a risk of the surgical tool crossing into the optical zone, which may be detrimental. On the other hand, too large of a transition zone may lead to a higher probability of fragmented tissue separating from the lenticule during extraction, as well as unnecessary removal of extra corneal tissue.

Therefore, in embodiments of the present invention, an added side extraction tab is integrated into the transition zone in the cutting pattern of the lenticule, to allow for a larger area to pull the tissue without crossing into the optical zone, while avoiding excessive removal of corneal tissue.

The side tab may improve speed of extraction, as well as completeness of extraction, i.e., to leave no lenticule tissue behind.

In the embodiments described above, the various incisions in the cornea may be performed using any suitable ophthalmic laser system. Described generally, such a laser surgical system includes a laser source for generating a pulse laser beam, an optical system for delivering the laser beam to a target tissue in the eye to form a focus spot therein, the optical system including a scanner system to scan the laser focus spot position in three dimensions, and a controller connected to above components to control and operate them. The laser surgical system preferably also includes measurement and imaging systems to measure and image the structure of the eye. The control system may include a processor executing computer-readable program code stored in a memory, where the program code causes the processor to control the scanner system to scan the laser focus spot according to pre-programmed scan patterns to form the various incisions described above.

A laser system that may be used to form the various incisions in embodiments of the present invention is described in more detail below with reference to FIGS. 3 and 4.

Figure 4:
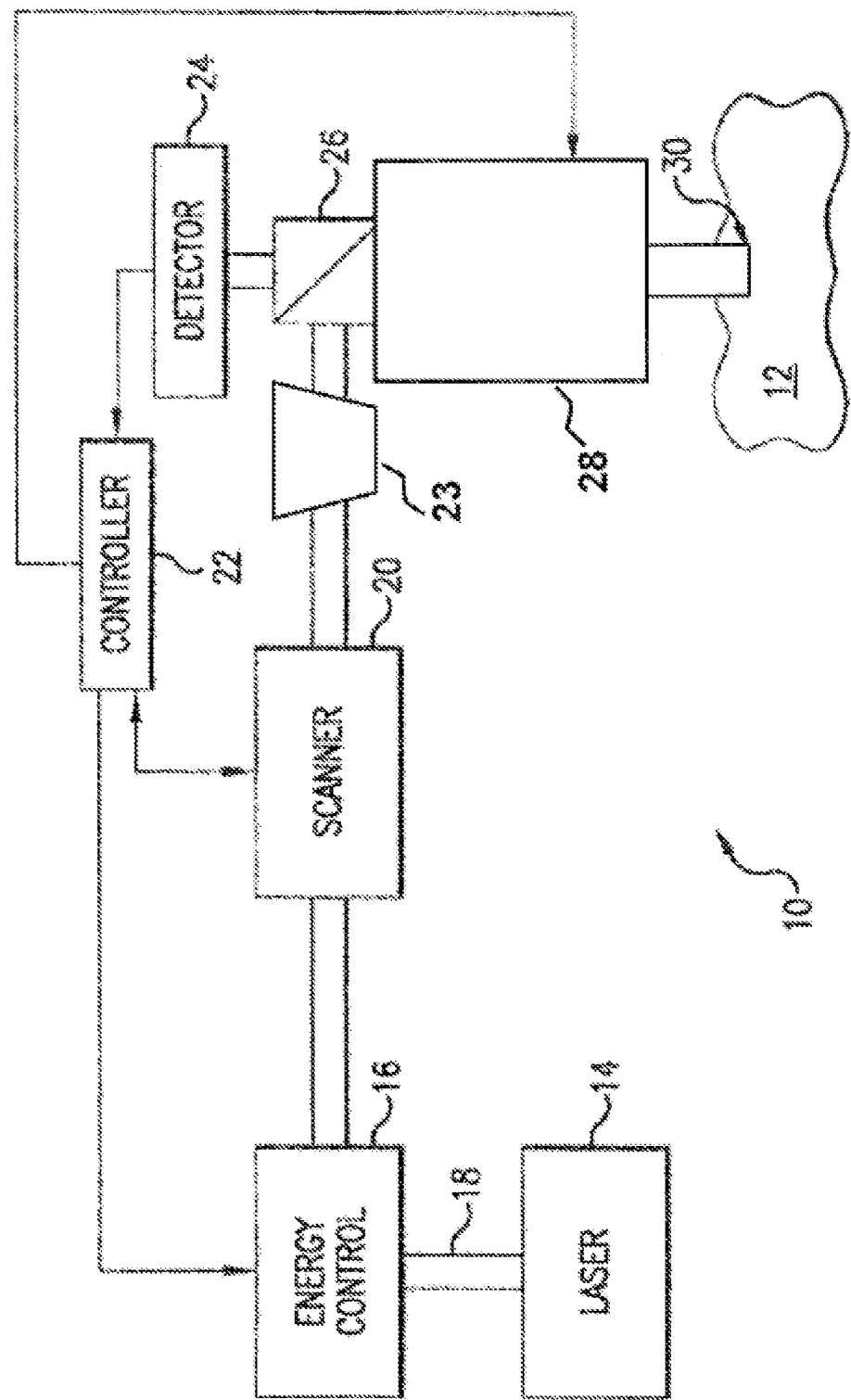
FIG. 4 is a simplified diagram of a surgical ophthalmic laser system that may be used to perform the corneal lenticule extraction methods according to embodiments of the present invention.

FIG. 4 shows a system 10 for making an incision in a material 12 such as the cornea. The system 10 includes, but is not limited to, a laser 14 capable of generating a pulsed laser beam 18, an energy control module 16 for varying the pulse energy of the pulsed laser beam 18, a Z-scanner 20 for modifying the depth of the pulse laser beam 18, a controller 22, a prism 23 (e.g., a Dove or Pechan prism, or the like), and an XY-scanner 28 for deflecting or directing the pulsed laser beam 18 from the laser 14 on or within the material 12. The controller 22, such as a processor executing suitable control software, is operatively coupled with the Z-scanner 20, the XY-scanner 28, and the energy control unit 16 to direct a scan line 30 of the pulsed laser beam along a scan pattern on or in the material 12. In this embodiment, the system 10 further includes a beam splitter 26 and a detector 24 coupled to the controller 22 for a feedback control mechanism (not shown) of the pulsed laser beam 18. Other feedback methods may also be used, including but not necessarily limited to position encoder on the scanner 20, or the like. In an embodiment, the pattern of pulses may be summarized in machine readable data of tangible storage media in the form of a treatment table. The treatment table may be adjusted according to feedback input into the controller 22 from an automated image analysis system in response to feedback data provided from an ablation monitoring system feedback system (not shown). Optionally, the feedback may be manually entered into the controller 22 by a system operator. The feedback may also be provided by integrating a wavefront measurement system (not shown) with the laser surgery system 10. The controller 22 may continue and/or terminate a sculpting or incision in response to the feedback, and may also modify the planned sculpting or incision based at least in part on the feedback. Measurement and imaging systems are further described in U.S. Pat. Nos. 6,315,413 and 8,260,024, the complete disclosures of which are incorporated herein by reference.

In an embodiment, the system 10 uses a pair of scanning mirrors or other optics (not shown) to angularly deflect and scan the pulsed laser beam 18. For example, scanning mirrors driven by galvanometers may be employed where each of the mirrors scans the pulsed laser beam 18 along one of two orthogonal axes. A focusing objective (not shown), whether one lens or several lenses, images the pulsed laser beam 18 onto a focal plane of the system 10. The focal point of the pulsed laser beam 18 may thus be scanned in two dimensions (e.g., the x-axis and the y-axis) within the focal plane of the system 10. Scanning along the third dimension, i.e., moving the focal plane along an optical axis (e.g., the z-axis), may be achieved by moving the focusing objective, or one or more lenses within the focusing objective, along the optical axis.

Laser 14 may comprise a femtosecond laser capable of providing pulsed laser beams, which may be used in optical procedures, such as localized photodisruption (e.g., laser induced optical breakdown). Localized photodisruptions can be placed at or below the surface of the material to produce high-precision material processing. For example, a micro-optics scanning system may be used to scan the pulsed laser beam to produce an incision in the material, create a flap of the material, create a pocket within the material, form removable structures of the material, and the like. The term "scan" or "scanning" refers to the movement of the focal point of the pulsed laser beam along a desired path or in a desired pattern.

In other embodiments, the laser 14 may comprise a laser source configured to deliver an ultraviolet laser beam comprising a plurality of ultraviolet laser pulses capable of photodecomposing one or more intraocular targets within the eye.

Although the laser system 10 may be used to photoalter a variety of materials (e.g., organic, inorganic, or a combination thereof), the laser system 10 is suitable for ophthalmic applications in some embodiments. In these cases, the focusing optics direct the pulsed laser beam 18 toward an eye (for example, onto or into a cornea) for plasma mediated (for example, non-UV) photoablation of superficial tissue, or into the stroma of the cornea for intrastromal photodisruption of tissue. In these embodiments, the surgical laser system 10 may also include a lens to change the shape (for example, flatten or curve) of the cornea prior to scanning the pulsed laser beam 18 toward the eye.

The laser system 10 is capable of generating the pulsed laser beam 18 with physical characteristics similar to those of the laser beams generated by a laser system disclosed in U.S. Pat. Nos. 4,764,930, 5,993,438, and U.S. patent application Ser. No. 12/987,069, filed Jan. 7, 2011, which are incorporated herein by reference.

Figure 5:
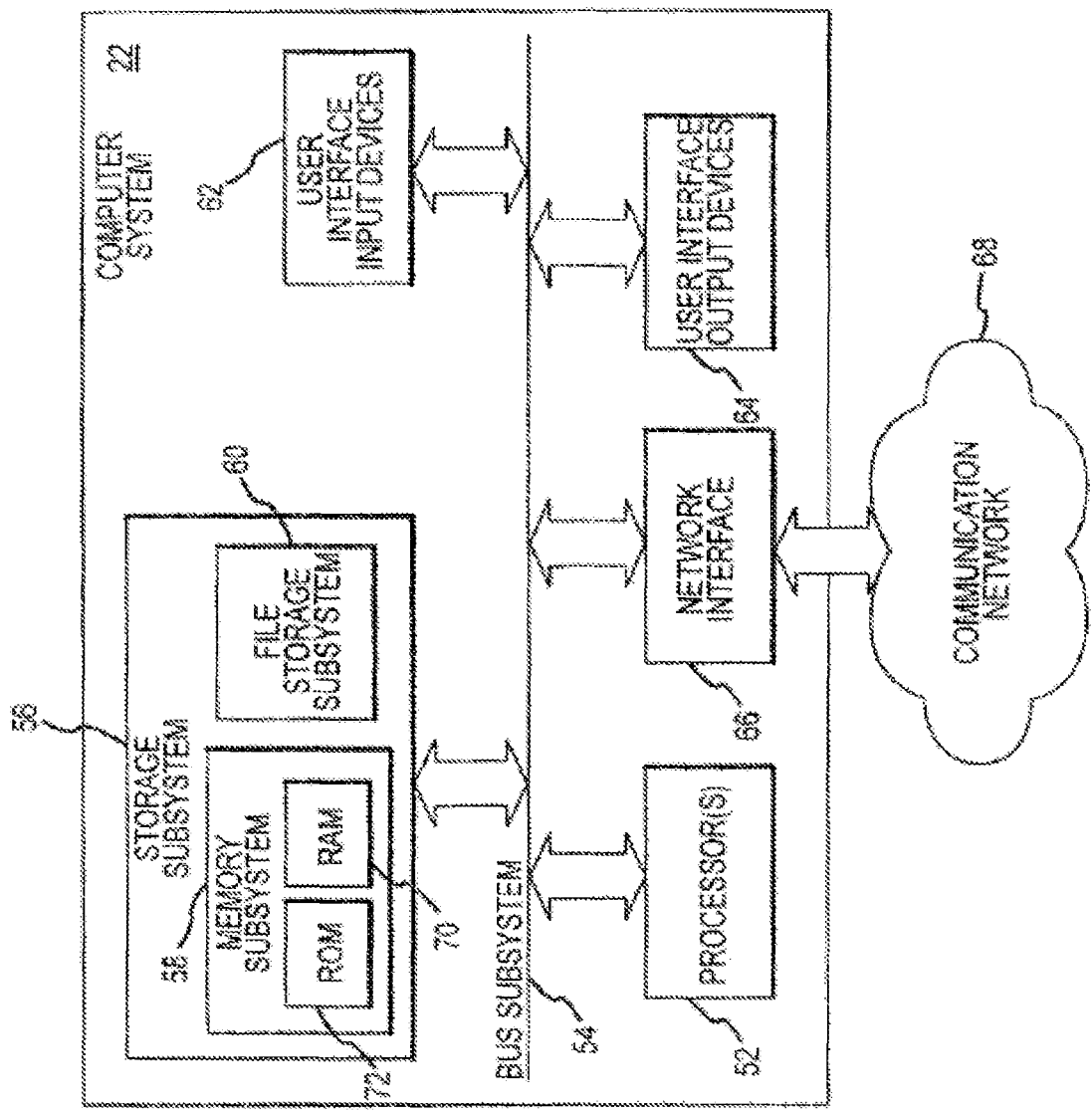
FIG. 5 is a simplified diagram of a controller of a surgical ophthalmic laser system that may be used to perform the corneal lenticule extraction methods according to an embodiment of the present invention.

FIG. 5 illustrates a simplified block diagram of an exemplary controller 22 that may be used by the laser system 10 according to an embodiment of this invention. Controller 22 typically includes at least one processor 52 which may communicate with a number of peripheral devices via a bus subsystem 54. These peripheral devices may include a storage subsystem 56, comprising a memory subsystem 58 and a file storage subsystem 60, user interface input devices 62, user interface output devices 64, and a network interface subsystem 66. Network interface subsystem 66 provides an interface to outside networks 68 and/or other devices. Network interface subsystem 66 includes one or more interfaces known in the arts, such as LAN, WLAN, Bluetooth, other wire and wireless interfaces, and so on.

User interface input devices 62 may include a keyboard, pointing devices such as a mouse, trackball, touch pad, or graphics tablet, a scanner, foot pedals, a joystick, a touch screen incorporated into a display, audio input devices such as voice recognition systems, microphones, and other types of input devices. In general, the term "input device" is intended to include a variety of conventional and proprietary devices and ways to input information into controller 22.

User interface output devices 64 may include a display subsystem, a printer, a fax machine, or non-visual displays such as audio output devices. The display subsystem may be a flat-panel device such as a liquid crystal display (LCD), a light emitting diode (LED) display, a touchscreen display, or the like. The display subsystem may also provide a non-visual display such as via audio output devices. In general, the term "output device" is intended to include a variety of conventional and proprietary devices and ways to output information from controller 22 to a user.

Storage subsystem 56 can store the basic programming and data constructs that provide the functionality of the various embodiments of the present invention. For example, a database and modules implementing the functionality of the methods of the present invention, as described herein, may be stored in storage subsystem 56. These software modules are generally executed by processor 52. In a distributed environment, the software modules may be stored on a plurality of computer systems and executed by processors of the plurality of computer systems. Storage subsystem 56 typically comprises memory subsystem 58 and file storage subsystem 60.

Memory subsystem 58 typically includes a number of memories including a main random access memory (RAM) 70 for storage of instructions and data during program execution and a read only memory (ROM) 72 in which fixed instructions are stored. File storage subsystem 60 provides persistent (non-volatile) storage for program and data files. File storage subsystem 60 may include a hard disk drive along with associated removable media, a Compact Disk (CD) drive, an optical drive, DVD, solid-state memory, and/or other removable media. One or more of the drives may be located at remote locations on other connected computers at other sites coupled to controller 22. The modules implementing the functionality of the present invention may be stored by file storage subsystem 60.

Bus subsystem 54 provides a mechanism for letting the various components and subsystems of controller 22 communicate with each other as intended. The various subsystems and components of controller 22 need not be at the same physical location but may be distributed at various locations within a distributed network. Although bus subsystem 54 is shown schematically as a single bus, alternate embodiments of the bus subsystem may utilize multiple busses.

Due to the ever-changing nature of computers and networks, the description of controller 22 depicted in FIG. 5 is intended only as an example for purposes of illustrating only one embodiment of the present invention. Many other configurations of controller 22, having more or fewer components than those depicted in FIG. 5, are possible.

As should be understood by those of skill in the art, additional components and subsystems may be included with laser system 10. For example, an imaging device or system may be used to guide the laser beam.

In an embodiment, the laser surgery system 10 includes a femtosecond oscillator-based laser operating in the MHz range, for example, 10 MHz, for example, from several MHz to tens of MHz. For ophthalmic applications, the XY-scanner 28 may utilize a pair of scanning mirrors or other optics (not shown) to angularly deflect and scan the pulsed laser beam 18. For example, scanning mirrors driven by galvanometers may be employed, each scanning the pulsed laser beam 18 along one of two orthogonal axes. A focusing objective (not shown), whether one lens or several lenses, images the pulsed laser beam onto a focal plane of the laser surgery system 10. The focal point of the pulsed laser beam 18 may thus be scanned in two dimensions (e.g., the X-axis and the Y-axis) within the focal plane of the laser surgery system 10. Scanning along a third dimension, i.e., moving the focal plane along an optical axis (e.g., the Z-axis), may be achieved by moving the focusing objective, or one or more lenses within the focusing objective, along the optical axis. It is noted that in many embodiments, the XY-scanner 28 deflects the pulse laser beam 18 to form a scan line.

In other embodiments, the beam scanning can be realized with a "fast-scan-slow-sweep" scanning scheme. The scheme consists of two scanning mechanisms: first, a high frequency fast scanner is used to produce a short, fast scan line (e.g., a resonant scanner); second, the fast scan line is slowly swept by much slower X, Y, and Z scan mechanisms.

All patents and patent applications cited herein are hereby incorporated by reference in their entirety.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While certain illustrated embodiments of this disclosure have been shown and described in an exemplary form with a certain degree of particularity, those skilled in the art will understand that the embodiments are provided by way of example only, and that various variations can be made without departing from the spirit or scope of the invention. Thus, it is intended that this disclosure cover all modifications, alternative constructions, changes, substitutions, variations, as well as the combinations and arrangements of parts, structures, and steps that come within the spirit and scope of the invention as generally expressed by the following claims and their equivalents.

What is claimed is:

1. A method for extracting a lenticule from a cornea of a patient's eye, comprising: to correct a vision of the patient's eye
    operating an ophthalmic surgical laser system to form a top lenticule surface incision in the cornea; and
    operating the ophthalmic surgical laser system to form a bottom lenticule surface incision in the cornea,
    wherein the top and bottom lenticule surface incisions intersect each other to form an isolated volume of corneal tissue between them, the isolated volume of corneal tissue being isolated from remaining portions of the cornea, and
    wherein the isolated volume of corneal tissue includes a lenticular portion having a circular or oval shape in a top view, and a side tab portion connected to the lenticular portion and protrudes from a peripheral location of the lenticular portion, wherein the side tab portion has a defined thickness profile in a side cross-sectional view; and extracting the isolated volume of corneal tissue from the patient's eye, whereby the vision of the patient's eye is corrected.

2. The method of claim 1, wherein the side tab portion has a length in a radial direction between 0.5 and 5 mm and a width in an angular direction between 0.5 and 3 mm in the top view.

3. The method of claim 1, wherein the side tab has a tapered thickness in the side cross-sectional view.

4. The method of claim 1, wherein both the top and bottom lenticule surface incisions have convex shapes, and wherein the side tab has a tapered shape in the side cross-sectional view.

5. The method of claim 4,
    wherein a central portion of the top lenticule surface incision is a part of a first sphere, and a peripheral portion of the top lenticule surface incision outside of the central portion has a steeper shape than the first sphere except in a portion corresponding to the side tab,
    wherein a central portion of the bottom lenticule surface incision is a part of a second sphere, and a peripheral portion of the bottom lenticule surface incision outside of the central portion has a steeper shape than the second sphere except in a portion corresponding to the side tab, and
    wherein the portions of the top and bottom lenticule surface incisions corresponding to the side tab have a less steep shape than the first and second spheres, respectively, in the side cross-sectional view.

6. The method of claim 1, wherein either the top lenticule surface incision or the bottom lenticule surface incision or both have convex shapes.

7. The method of claim 1, wherein each of the top and bottom lenticule surface incisions is a smooth surface.

8. The method of claim 1, further comprising operating the ophthalmic surgical laser system to form an entry cut in the cornea, the entry cut having a band shape extending from an anterior surface of the cornea to intersect the top or bottom lenticule surface incision, wherein the intersection of the entry cut with the top or bottom lenticule surface incision is in a vicinity of the side tab in the top view.

9. The method of claim 1, further comprising, before forming the top and bottom lenticule surface incisions, coupling the eye to a patient interface device, wherein the cornea contacts a surface of the patient interface device and conforms to a shape of the surface.

10. An ophthalmic surgical laser system comprising:
    a laser system configured to generate a pulsed laser beam;
    an optical delivery system configured to deliver the pulsed laser beam to a cornea of a patient's eye, including a scanner system configured to scan a focus spot location of the pulsed laser beam within the cornea;
    a controller configured to control the laser system and the scanner system to:
        scan the focus spot location of the pulsed laser beam within the cornea to form a top lenticule surface incision in the cornea; and
        scan the focus spot location of the pulsed laser beam within the cornea to form a bottom lenticule surface incision in the cornea, wherein the top and bottom lenticule surface incisions intersect each other to form an isolated volume of corneal tissue between them, the isolated volume of corneal tissue being isolated from remaining portions of the cornea, and wherein the isolated volume of corneal tissue includes a lenticular portion having a circular or oval shape in a top view, and a side tab portion connected to the lenticular portion and protrudes from a peripheral location of the lenticular portion, wherein the side tab portion has a defined thickness profile in a side cross-sectional view; and wherein the isolated volume of corneal tissue is configured to be extracted from the patient's eye to correct a vision of the patient's eye.

11. The laser system of claim 10, wherein the side tab portion has a length in a radial direction between 0.5 and 5 mm and a width in an angular direction between 0.5 and 3 mm in the top view.

12. The laser system of claim 10, wherein the side tab has a tapered thickness in the side cross-sectional view.

13. The laser system of claim 10, wherein both the top and bottom lenticule surface incisions have convex shapes, and wherein the side tab has a tapered shape in the side cross-sectional view.

14. The laser system of claim 13,
wherein a central portion of the top lenticule surface incision is a part of a first sphere, and a peripheral portion of the top lenticule surface incision outside of the central portion has a steeper shape than the first sphere except in a portion corresponding to the side tab, wherein a central portion of the bottom lenticule surface incision is a part of a second sphere, and a peripheral portion of the bottom lenticule surface incision outside of the central portion has a steeper shape than the second sphere except in a portion corresponding to the side tab, and wherein the portions of the top and bottom lenticule surface incisions corresponding to the side tab have a less steep shape than the first and second spheres, respectively, in the side cross-sectional view.

15. The laser system of claim 10, wherein either the top lenticule surface incision or the bottom lenticule surface incision or both have convex shapes.

16. The laser system of claim 10, wherein each of the top and bottom lenticule surface incisions is a smooth surface.

17. The laser system of claim 10, wherein the controller is further configured to control the laser system and the scanner system to form an entry cut in the cornea, the entry cut having a band shape extending from an anterior surface of the cornea to intersect the top or bottom lenticule surface incision, wherein the intersection of the entry cut with the top or bottom lenticule surface incision is in a vicinity of the side tab in the top view.

18. The laser system of claim 10, further comprising a patient interface device configured to be coupled to the eye, the patient interface device including a contact surface configured to contact an anterior surface of the cornea.

* * * * *